United States Patent
Suzuki

(10) Patent No.: US 9,551,678 B2
(45) Date of Patent: Jan. 24, 2017

(54) DISPLAY DEVICE

(71) Applicant: Japan Display Inc., Tokyo (JP)

(72) Inventor: Takayasu Suzuki, Tokyo (JP)

(73) Assignee: Japan Display Inc., Tokyo (JP)

( * ) Notice: Subject to any disclaimer, the term of this patent is extended or adjusted under 35 U.S.C. 154(b) by 0 days.

(21) Appl. No.: 14/732,621

(22) Filed: Jun. 5, 2015

(65) Prior Publication Data

US 2015/0362449 A1 Dec. 17, 2015

(30) Foreign Application Priority Data

Jun. 13, 2014 (JP) ................................ 2014-122056

(51) Int. Cl.
*H01L 27/32* (2006.01)
*G01N 27/12* (2006.01)
*H01L 51/52* (2006.01)

(52) U.S. Cl.
CPC ......... *G01N 27/121* (2013.01); *H01L 51/5246* (2013.01); *H01L 27/3244* (2013.01)

(58) Field of Classification Search
CPC .. H01L 27/32; H01L 27/3244; H01L 27/3274; H01L 51/5246; H01L 51/3271; H01L 51/524
See application file for complete search history.

(56) References Cited

U.S. PATENT DOCUMENTS

| | | | |
|---|---|---|---|
| 2014/0103312 A1* | 4/2014 | Huang | H01L 51/5246 257/40 |
| 2014/0145588 A1* | 5/2014 | Oh | H01L 51/524 313/512 |
| 2014/0291629 A1* | 10/2014 | Kim | H01L 27/3274 257/40 |
| 2015/0372253 A1* | 12/2015 | Hong | H01L 51/524 257/40 |

FOREIGN PATENT DOCUMENTS

| | | |
|---|---|---|
| JP | 2003-157970 A | 5/2003 |
| JP | 2010-160905 A | 7/2010 |

OTHER PUBLICATIONS

Korean Office Action mailed on Sep. 5, 2016 for corresponding Korean Application No. 10-2015-0077795 with partial translation.

* cited by examiner

*Primary Examiner* — Phuc Dang
(74) *Attorney, Agent, or Firm* — Typha IP LLC

(57) ABSTRACT

A display device includes a first substrate provided with a pixel circuit in a display region, a second substrate provided facing the first substrate, a dam agent bonding the first substrate and the second substrate and sealing the display region, and a moisture detection part provided between a first region provided with the dam agent and the display region.

11 Claims, 6 Drawing Sheets

DISPLAY DEVICE

CROSS REFERENCE TO RELATED APPLICATIONS

This application is based upon and claims the benefit of priority from the prior Japanese Patent Application No. 2014-122056, filed on Jun. 13, 2014, the entire contents of which are incorporated herein by reference.

FIELD

The present invention is related to a display device. In particular, the present invention is related to sealing of a display device using an organic electroluminescence (EL) phenomenon.

BACKGROUND

Thin display devices using liquid crystals or an organic EL phenomenon are being used. In particular, display devices using an organic EL phenomenon are different to those using liquid crystals since it is possible to display vivid images because they are light emitting. In addition, in recent years flexible display devices are being developed by using materials such as flexible substrates.

For example, it is possible to exemplify Japanese Laid Open Patent 2003-157970 as a technology related to a display device using an organic EL phenomenon. The display device disclosed in this document is provided with an organic EL device provided above a glass substrate, a sealing component adhered to the top of the glass substrate via an adhesive and covering the organic EL device, and an indicator which changes color by adsorbing moisture in regions apart from a display region above a glass substrate In a display device which uses an organic EL phenomenon, it can not be said that an organic EL device includes sufficient resistance to moisture or oxygen. As a result, sealing structure is provided on a substrate when assembling a display device so that moisture or oxygen does not enter the interior from the exterior.

However, even when sealing is performed, it is difficult to completely prevent moisture from entering after manufacture of a display device which sometimes leads to a deterioration or damage to a display.

Therefore, the present invention proposes a display device which can detect the infiltration of moisture before deterioration or damage to a display occurs.

SUMMARY

According to one embodiment of the present invention, a display device comprising a first substrate provided with a pixel circuit in a display region, a second substrate provided facing the first substrate, a dam agent bonding the first substrate and the second substrate and sealing the display region, and a moisture detection part provided between a first region provided with the dam agent and the display region.

DESCRIPTION OF EMBODIMENTS

Pluralities of embodiments for realizing the present invention are explained below while referring to the diagrams. Furthermore, the present invention is not limited to these embodiments and can be realized by various modifications. In addition, in the diagrams, the scale of up and down and left and right are not necessarily the same and width and thickness are sometimes shown exaggerated.

First Embodiment

Figure 1A:
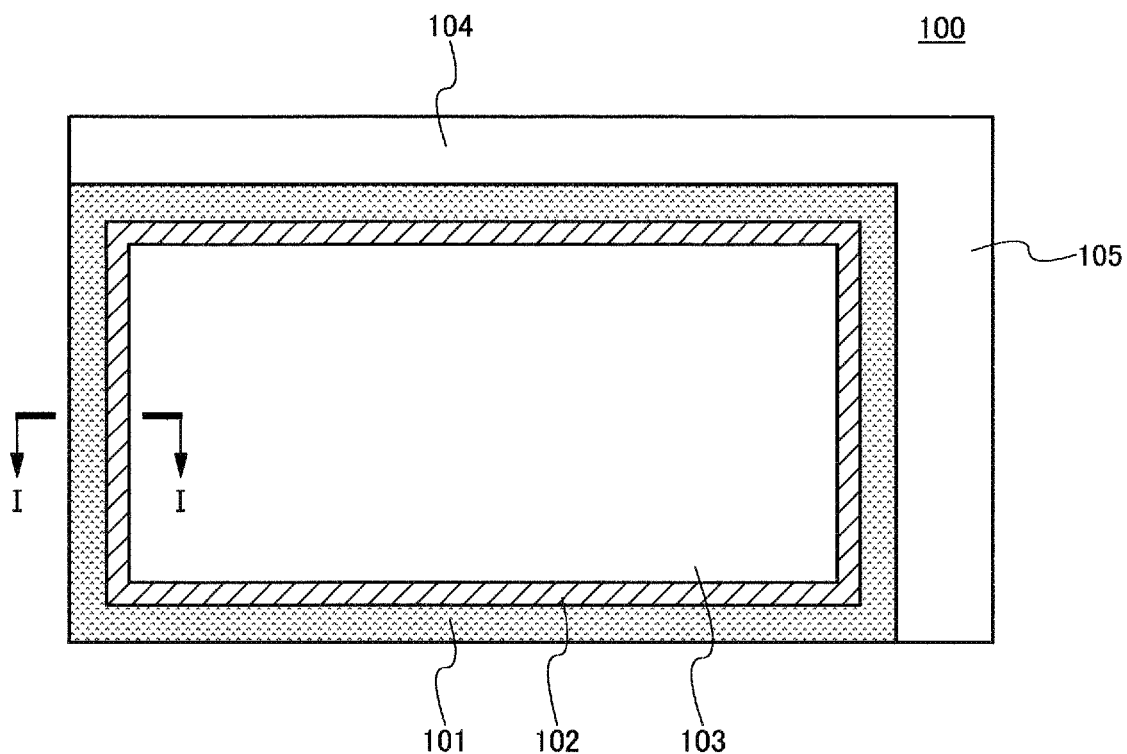
FIG. 1A shows an upper surface view of a display device related to one embodiment of the present embodiment.
Figure 1B:
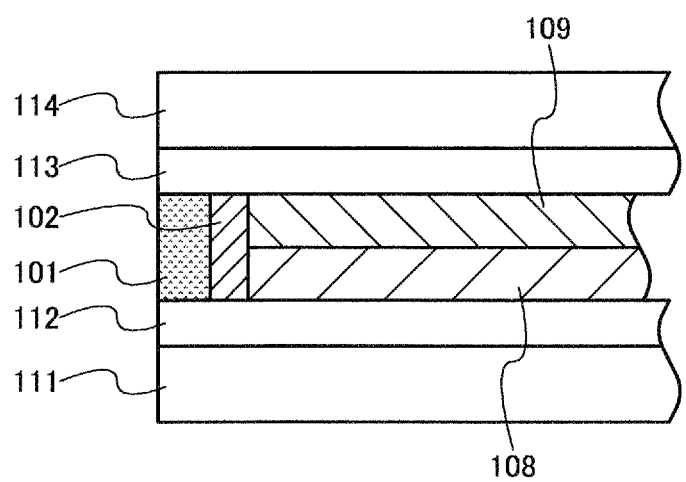
FIG. 1B shows a cross-sectional view of a display device related to one embodiment of the present embodiment.

FIG. 1A shows an upper surface view of a display device related to the first embodiment of the present invention, and FIG. 1B shows a cross-sectional view along the line I-I in FIG. 1A.

As is shown in FIG. 1A, the display device 100 has a square or rectangular shape seen from an upper surface. However, in the present embodiment it is possible to use an arbitrary geometric shape as the shape of the display device 100.

The display device related to the present embodiment is formed by bonding together opposing substrates as is shown in FIG. 1B. Here, the opposing substrates are substrate 111 and substrate 114. Furthermore, it is possible to form a barrier layer 112 above the substrate 111 according to necessity. In the present embodiment, depending on necessity a substrate formed with a barrier layer 113 is treated as one integral unit and is sometimes referred to simply as "substrate". In particular, a lower side substrate in FIG. 1B is sometimes referred to as "first substrate". A substrate facing the "first substrate" is sometimes referred to as "second substrate".

It is possible to use a substrate using glass for example as the substrate 111. In particular, by making the thickness of the glass substrate thin, it is possible to bend the substrate. In addition, it is also possible to use a resin substrate such as polyimide apart from a glass substrate. In this case, it is possible to use a transparent material in the case where an image is displayed on the substrate 111 side.

Although the barrier layer 112 is not essential, in the case where the substrate 111 has a property for allowing moisture or oxygen to pass through, it is used so that moisture or oxygen does not reach a display element used in a display device. For example, the barrier layer 112 is formed using a high density transparent metal oxide. Generally, in the case of moisture, the barrier layer 112 is formed using a material having transparent properties of around $10^{-6}$ g/m²/day.

A display circuit for displaying an image is formed in the display region 103 shown in FIG. 1A. Referring to the cross-sectional view in FIG. 1B, including the organic EL device the display region 103 includes a fourth region 108 formed with a display circuit and a fifth region filled 109 with a filler.

Figure 2A:
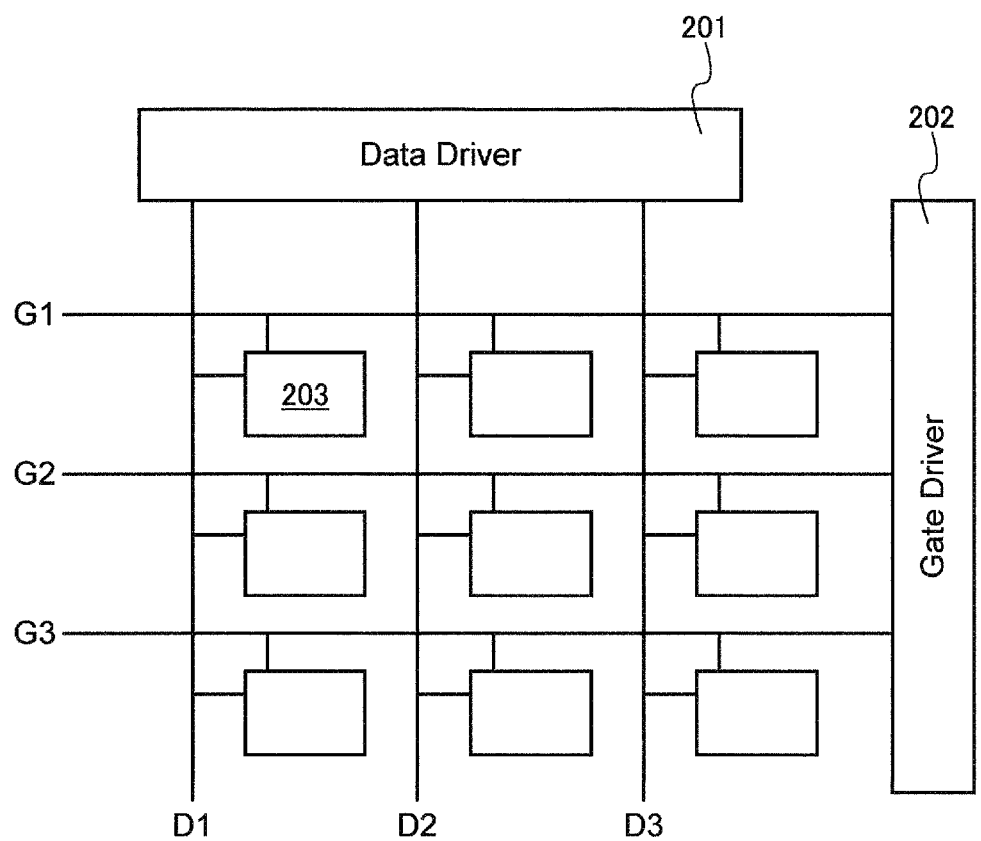
FIG. 2A shows a display circuit of a display device related to one embodiment of the present embodiment.

FIG. 2A shows an example of a display circuit. A plurality of data lines D1, D2 and D3 are connected to a data driver 201, and a plurality of gate lines G1, G2, G3 are connected to a gate driver 202. Furthermore, the number of data lines connected to the data driver 201 and the number of gate lines connected to the gate driver 202 do not have to be the same and can be an arbitrary number.

Furthermore, the data driver 201 and gate driver 202 can be provided in an upper end part 104 of the display device and a right end part 105 of the display device.

A pixel circuit 203 is provided corresponding to an intersection point between each of the plurality of data lines and each of the plurality of gate lines respectively.

Figure 2B:
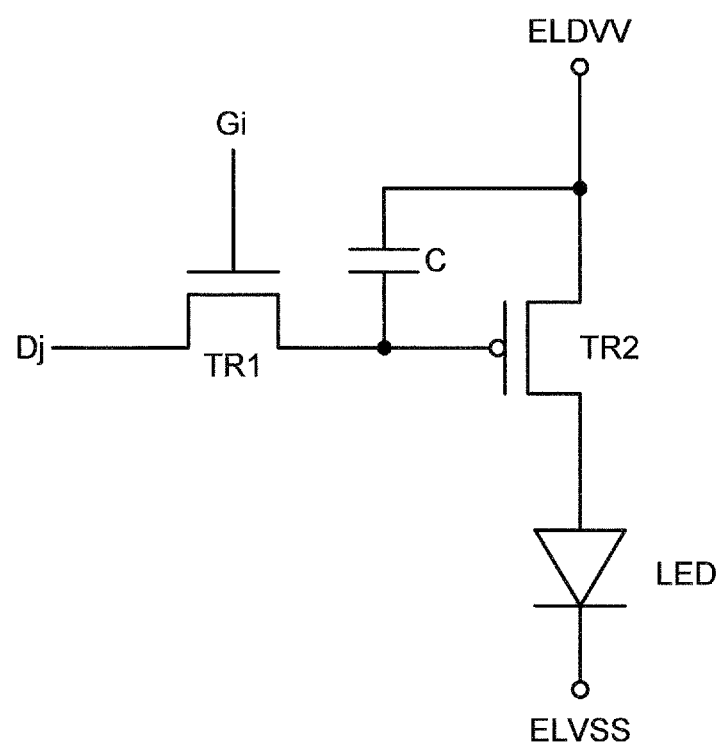
FIG. 2B shows a pixel circuit of a display device related to one embodiment of the present embodiment.

FIG. 2B shows an example of a pixel circuit 203. One of either a drain electrode or source electrode of a switching device TR1 is connected to a data line Dj, and the other is connected to one electrode of a condenser C and a gate electrode of a control transistor TR2. A gate line G1 is connected to the gate electrode of the switching device TR1.

The other electrode of the condenser C and either the drain electrode or source electrode of the control transistor TR2 are connected to a power supply line ELDVV, the other of the drain electrode or source electrode of the control transistor TR2 is connected to an anode electrode of an organic EL device LED, and the cathode electrode of the organic EL device LED is connected to a power supply line ELVSS.

When the voltage of the gate line Gi becomes large and the switching device TR1 is switched ON, a voltage of data signal supplied to the data line Dj is accumulated in the condenser C. Following this, when the voltage of the gate line Gi becomes small and the switching device TR1 is switched OFF, a current amount flowing to the power supply line ELVSS from the power supply line DLDVV via the organic EL device LED is controlled via the control transistor TR2 according to a voltage value of the data signal accumulated in the condenser C.

The organic EL device LED is formed from a hole transport layer, light emitting layer and electron transport layer, molecule are excited by energy generated by coupling of the holes and electrons in the light emitting layer and the excited molecule emit light by the energy discharged when returning to a ground state.

Furthermore, a display device formed with a pixel using an organic EL device was explained above. However, the present invention is not limited to a display device formed with a pixel using an organic EL device. For example, it is also possible to apply the present invention to a display device using liquid crystals.

The first region 110 shows a region provided with a dam agent. This region can be provided in an end part of the substrate 111 except an upper end part 104 and right end part in which the data driver 201 and gate driver 202 are provided. The dam agent is an epoxy resin including thermosetting properties or ultraviolet curable properties for example. The dam agent is provided in the first region 101 of FIG. 1A using a dispenser or similar equipment (not shown in the diagram). The thickness of the dam agent when being provided using a dispenser exceeds the thickness of a display circuit of 10 μm or more and 500 μm or less for example. In addition, the viscosity of the dam agent can be set for example at 1000 mPas or more and 100 Pas or less.

A moisture detection part is provided on the inner side of the first region 101 in which the dam agent provided and in the second region 102 on the outer side of the display region 103. It is possible to use a material which emits colors and light when exposed to moisture for example as the moisture detection part. This material can be provided by mixing with a dam agent material for example. In this way, it is possible to supplement the adhesive strength of the dam agent provided in the first region 101.

It is possible to use an anthocyanin group material or calcium as the material which emits color when exposed to moisture. In addition, it is possible to use cobalt chloride. It is possible to use a material which emits light by a luminol reaction or cyalume reaction as the material which emits light when exposed to moisture.

In the present embodiment, the reason for provided a moisture detection part in the second region 102 on the inner side of the first region 101 is that when a moisture detection part is provided in the first region 101, it is possible to expose the moisture detection part to the side surface of the display device 100 and although moisture does not infiltrate the interior of the display device 100, the moisture detection part emits colors or emits light which prevents an error in detecting moisture. That is, the moisture detection part is provided in the second region 102 on the inner side of the first region 101 so that the moisture detection part emits colors or emits light when moisture actually infiltrates the interior of the display device 100. The second region 102 in which the moisture detection part is provided is preferred to contact both the substrate 111 (or barrier layer 112) and the substrate 114 (or barrier layer 113) along the first region 101 in which the dam agent is provided. By adopting this structure, it is possible to ensure detection not only of moisture infiltrating through a dam agent but also moisture infiltrating through a boundary between the dam agent and substrate (or barrier layer).

After the dam agent is provided in the first region 101 and the moisture part is provided in the second region 102, a filler agent is filled into a fifth region in the display region 103, a substrate 114 having a barrier layer 113 is provided if necessary, the dam agent and filler agent are cured and sealing is performed.

Furthermore, in the case where the pixel circuit performs top emission type light emitting, since an image is displayed via the substrate 114 which faces the substrate 111, a transparent material is used for the substrate 114 and the barrier layer 113 provided if necessary. In this way, even if the substrate 111 is opaque, visibility is desired to be ensured by being transparent for parts of the substrate 111 in regions in which at least the moisture detection part is provided.

In addition, in the case where the pixel circuit performs bottom emission type light emitting, since an image is displayed via the substrate 111, a transparent material is used for the substrate 111 and the barrier layer 113 provided if necessary. In this way, it is possible to detect color being emitted or light being emitted by the moisture detection part from the substrate 111. In addition, even if the substrate 114 is opaque, visibility is desired to be ensured by being transparent for parts of the substrate 114 in regions in which at least the moisture detection part is provided.

Furthermore, although it was explained above that a material which emits color or emits light when exposed to moisture is used for the moisture detection part, the present invention is not limited to this. For example, it is possible to use a material in which electrical resistance changes when exposed to moisture. For example, it is possible to use a material which separates into ions and electrical resistance drops when moisture is absorbed. In this way, it is possible form an electrode and wiring in advance in the substrates 111 and 114 and measure the electrical resistance of a material in which electrical resistance changes when exposed to moisture. In this way, it is possible to display a warning when moisture is detected.

As described above, according to the present invention it is possible to detect moisture which has infiltrated the interior of a display device 100 and predict a deterioration in or damage to a display.

Second Embodiment

Figure 3A:
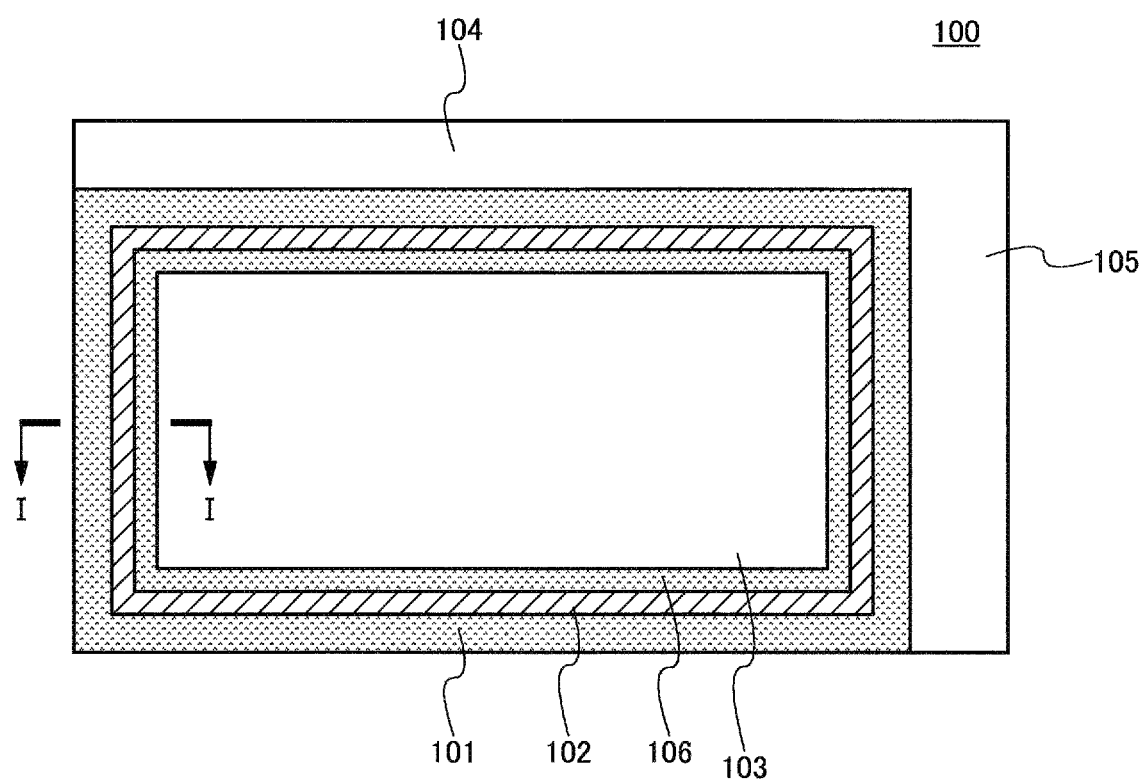
FIG. 3A shows an upper surface view of a display device related to one embodiment of the present embodiment.
Figure 3B:
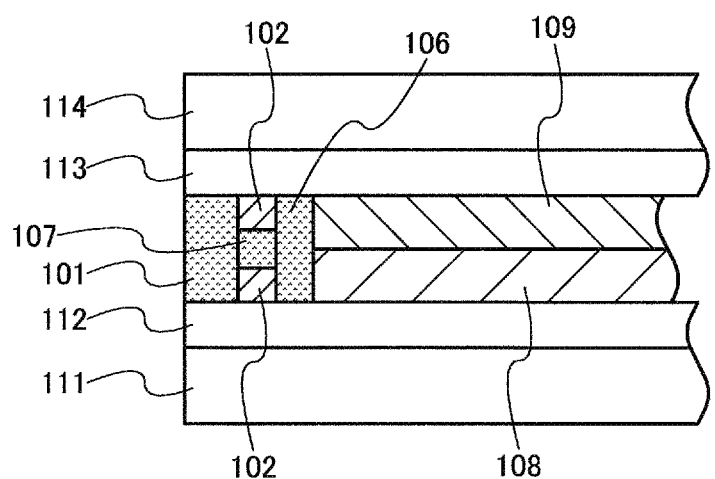
FIG. 3B shows a cross-sectional view of a display device related to one embodiment of the present embodiment.

FIG. 3A shows an upper surface view of a display device related to a second embodiment of the present invention. FIG. 3B shows a cross-sectional view of the display device along the line I-I in FIG. 3A.

As is shown in FIG. 3A, a display device 200 seen from an upper surface is formed in a square shape or rectangular shape. However, in the present embodiment, the point where it is possible to use an arbitrary geometric shape as the shape of the display device 200 is the same as in the first embodiment.

In addition, being able to arrange a barrier layer 112 in the substrate 112 and a barrier layer 113 in the substrate 114 is the same as in the first embodiment.

The different points between the present embodiment and the first embodiment is that as is shown in FIG. 3A and FIG. 3B, a dam agent is provided in the first region 101, a second region 102 provided with a moisture detection part is provided therein, and a third region 106 provided with a dam agent is included on the inner side of the second region 102. That is, the second region 102 provided with a moisture detection part is sandwiched between the first region 101 provided with the dam agent and the third region 106. Furthermore, a display region 103 provided with a pixel circuit is provided in the interior of the third region 106.

In this way, in the present embodiment, by sandwiching a moisture detection part between a first region 101 provided with a dam agent and a third region 106, it is possible to increase the purity of the material of the moisture detection part and reduce the detection limitations when detection moisture. That is, it is possible to increase the sensitivity of moisture detection.

In addition, there are many cases where moisture passes more through a contact surface between a dam agent and an upper and lower substrate 111 (barrier layer 112 according to necessity) and substrate 114 (barrier layer 113 according to necessity) than through the interior of the dam agent. Thus, as is shown in FIG. 3B, it is possible include a first moisture detection surface which contacts the substrate 111 (including the barrier layer 112 if necessary) and a second moisture detection surface which contacts the substrate 114 (including the barrier layer 113 if necessary). In addition, it is possible to arrange a component 107 between and contacting with the substrate 111 (including the barrier layer 112 if necessary) and substrate 114 (including the barrier layer 113 if necessary). In this way, it is possible to minimize the amount of material of the moisture detection part and maximize the detection capability of moisture. Furthermore, although it is possible to use a dam agent for example as the component 107, the present invention is not limited to this. For example, a metal plate may also be used. In particular, a metal which forms such a plate can be used for reflecting light. In this way, it is possible to more easily detect emitted color or emitted light of the moisture detection part. In particular, the metal is not limited as long as the metal includes properties for reflecting light.

What is claimed is:

1. A display device comprising:
a first substrate provided with a pixel circuit in a display region;
a second substrate provided facing the first substrate;
a dam agent bonding the first substrate and the second substrate and sealing the display region; and
a moisture detection part provided between a first region provided with the dam agent and the display region,
wherein the moisture detection part comprises a mixture of a coloring or light emitting material to a material of the dam agent, and the coloring or light emitting material is coloring or light emitting in response to moisture.

2. The display device according to claim 1, wherein the moisture detection part including a material of electrical resistance changes in response to moisture.

3. The display device according to claim 1, wherein a second region provided with the dam agent is provided between the moisture detection part and the display region.

4. The display device according to claim 3, wherein the moisture detection part including a material of electrical resistance changes in response to moisture.

5. The display device according to claim 3, wherein the moisture detection part including a first moisture detection surface contacting the first substrate and a second moisture detection surface contacting the second substrate, and a component for dividing the first moisture detection surface and the second moisture detection surface is provided between the first moisture detection surface and the second moisture detection surface.

6. The display device according to claim 5, wherein the component includes a property for reflecting light.

7. The display device according to claim 1, wherein the moisture detection part is included a coloring or light emitting material, and the coloring or light emitting material is coloring or light emitting in response to moisture.

8. The display device according to claim 1, wherein the moisture detection part contacting the first substrate and the second substrate.

9. The display device according to claim 1, wherein at least one of the first substrate or the second substrate is transparent in the moisture detection part.

10. The display device according to claim 1 wherein the first substrate and the second substrate comprises a resin.

11. The display device according to claim 1, wherein the pixel circuit is provided with an organic EL device in a pixel.

* * * * *